United States Patent [19]

Brubaker

[11] Patent Number: 5,180,661

[45] Date of Patent: Jan. 19, 1993

[54] PLATELET CROSS MATCHING

[75] Inventor: Daniel B. Brubaker, Redondo Beach, Calif.

[73] Assignee: Rei, Inc., Torrance, Calif.

[21] Appl. No.: 167,542

[22] Filed: Mar. 14, 1988

[51] Int. Cl.$^5$ .................. G01N 33/545; G01N 33/563
[52] U.S. Cl. .................. 435/7.21; 435/7.24; 435/7.95; 435/21; 435/180; 435/975; 436/512; 436/531; 436/809
[58] Field of Search .............. 424/11; 435/7, 7.21, 435/180, 7.95, 810, 975, 7.24; 436/512, 531, 809; 427/2

[56] References Cited

U.S. PATENT DOCUMENTS

| | | | |
|---|---|---|---|
| 4,132,746 | 1/1979 | Urry et al. | 528/328 |
| 4,275,053 | 6/1981 | Rosenfield et al. | 436/531 |
| 4,717,654 | 1/1988 | Savoca et al. | 436/518 |
| 4,810,632 | 9/1989 | McMillan | 436/507 |

OTHER PUBLICATIONS

Horai et al., Immunol. Lett; 3, 67–72, 1981.
Biotechnology Catalogue of Fischer Scientific Co., 1983, p. 97, Gudino et al., Blood, 57, 32–37, 1981.
Sintnicolaas et al., British Journ. Haematol., 66, 363–367, 1987.
Schiffer et al., Blood, 61, 311–317, 1983.
Tamerius et al., Blood, 62, 744–749, 1983.
D. B. Brubaker et al., American Journal of Hematology, 24, 375–387, 1987.

Primary Examiner—David Saunders

[57] ABSTRACT

A method and kit for typing platelets in whole blood for human leucocyte antigens (HLA). A panel of HLA antigens is made on a microtiter plate. Each well is contacted with serum to be typed and the amount of reaction is followed with anti-human (Fab '2) alkaline phosphatase and disodium p-phenylphosphate.

2 Claims, No Drawings

PLATELET CROSS MATCHING

BACKGROUND OF THE INVENTION

1. Field of the Invention

This invention relates to blood typing methods, particularly those methods for typing platelets, more particularly those methods using an Enzyme Linked Immunospecific Assay (hereinafter ELISA) techniques.

2. Relevant Art

Blood contains many factors that are immunologically distinct. Among these are the well known ABO system, but other factors in blood have types as well. In particular, platelets have antibodies associated with them that are distinct immunologically. Patients who are undergoing many repeated transfusions may develop resistance to certain types of platelets. Resistance to platelets results in destruction of platelets. Therefore, typing the platelets before the transfusion could avoid an immune response. In particular, immune response and the likelihood of transplant rejection in major surgery, for example, kidney transplants and the like, can be reduced.

One set of antigens known to be present on the surface of platelets are the human leucocyte antigens (HLA). Matching HLA's correctly predicts platelet crossmatching in about 60%-80% of cases. A variety of methods have been used that achieve the high success ratio, including flourescence, radio labeled anti-globulin test, and solid phase red cell adherence test. However, these techniques are time consuming and require specialized equipment and specially trained personnel, or in the case of the solid phase red cell adherence test, they lack specificity.

Kakaiya, et al. (Transfusion 24, page 35 (1984)) used an ELISA technique for platelet cross-matching. However, it gave low sensitivity and specificity.

It would be advantageous to have an ELISA test for crossmatching platelets that would be sensitive and specific, because ELISA is convenient and requires fewer pieces of specialized equipment.

SUMMARY OF THE INVENTION

An aspect of this invention is a method to assay platelets for HLA comprising the steps of:

forming a plurality of microtiter test wells, each well containing an antigen to one type of HLA adhering to the bottom surface of the well, and the plurality of wells containing antigens to more than one type of HLA;

contacting a potential blood recipient's serum with the bottom surface of the plurality of test wells;

decanting the serum;

contacting the plurality of test wells with (Fab '2) Anti-human IgG conjugate alkaline phosphatase;

adding a p-nitrophenol phosphate to each well; and determining the optical densities of the wells.

A further aspect of this invention is a kit for assaying platelets, comprising:

a microtiter plate having a plurality of wells each containing one type of HLA adhering to the bottom of the wall; and a supply of (Fab '2) anti-human IgG conjugate alkaline phosphatase.

DETAILED DESCRIPTION OF THE INVENTION

Platelets can have a variety of antibodies attached to their cell membranes. Among those antibodies are platelet specific antibodies and human leukocyte antigen (HLA) antibodies. The various distinguishable antibodies will be referred to herein as "types." It is known that if whole blood is typed for HLA the incidence of alloimmunization and related problems can be dramatically reduced.

HLA can be typed using ELISA by several methods. A first perferred method is the creation of microtiter wells containing monolayers of platelets. Potential recipient blood is typed by ELISA techniques. When this approach is used various antigens on the surface of the platelets, for example, platelet specific antigens, must be somehow neutralized so they don't interfer with the test results.

A second preferred method is coating the bottoms of microtiter wells with previously extracted HLA antigens. Again, the potential recipient blood is typed by ELISA techniques.

It is especially preferred to use whole platelets on a first microtiter plate and HLA in a second microtiter plate. These results then cross check. The preferred ELISA technique is to add the human test serum from a potential recipient, decant the excess liquid, and contact the well with (Fab '2) anti-human IgG alkaline phosphatase and then measuring the amount with disodium p-phenylphosphate pNp. The use of the (Fab '2) fragment decreases non-specific binding with FC receptors, which are missing in the case of the (Fab '2) fragment. (Fab '2) IgG peroxidase can also be advantageously used.

The first microtiter plate is made as follows: Platelets are collected from donors with known HLA types. Blood is collected in an anticoagulent, preferably ACD-A, and then the platelet-rich plasma (PRP) is obtained by centrifuging the whole blood, for example, at 1030g for five minutes. The upper two-thirds of the PRP is aspirated and centrifuged, for example, at 830 g for ten minutes.

The platelet button is then harvested. It is preferred that the platelets be washed in a modified Tyrodes solution containing 1.5 mg/ml of 1-cyclohexyl-3-(2-morpholinoethyl)carbodiimide metho-p-toluenesulfonate (hereinafter CDI). After washing the platelet count is adjusted to 60000 platelets per $mm^3$. Then sixty microliters of solution is placed in each microtiter well, thereby creating monolayers of platelets on the bottom of each well. The wells on the microtiter plate contain different types of HLA platelets, but it is preferred that at least four wells contain platelets of any given type.

The CDI enhances the bond between the bottom of each well and the glycoproteins on the cell walls of the platelets. The formation of a platelet monolayer on the bottom of the microtiter wells is critical to the success of this invention.

The microtiter plates thus prepared can be prepared for long term storage. The plate is treated with a freezing solution, preferably dimethyl sulfoxide (DMSO), heat-inactivated fetal calf serum, and Veronal buffer-ethylene diamine tetraacetic acid (EDTA) and frozen for later use.

It is important to distinguish between HLA antigens' and platelet specific antigens and prevent nonspecific antibody binding by the Fc receptor on platelets. The binding of the platelet non-specific antibodies can be reduced by contacting platelets with a bacterial suspension. The platelets are disrupted by contacting them with Tween - 100 or 1% non-ionic detergent, preferably Noridet P-40 or Triton X-100. Then a formalin fixed protein A containing staphylococcus aureus in approximately 10% suspension is centrifuged and the bacterial suspension pellet is resuspended in 1 ml of the platelet lysate. It is preferred to wash the bacterial suspension with phosphate buffered saline at pH5 (PBS) before centrifugation. After approximately thirty minutes, the bacteria are centrifuged out of the lysate. Platelets prepared in this manner have decreased non-specific binding.

Ten microliters of monoclonal antibody 5FI is added to eight wells. Ten microliters of monoclonal antibody P2 is added to three wells as a control. 100 microliters of lysate is added to each well and incubated at 4° C for 60 minutes. The wells are then washed three times with PBS containing 0.5% Nonidet P-40. The glycoprotein IIB IIIa attaches to monocolonal antibody P2. This glycoprotein contains most all of the platelet specific antigens which will determine any of these antibodies in patients. Monoclonal antibody 5Fl attaches to glycoprotein lb which has no antigenic specificity, binding the platelet lysate to the wells, exposing IIa IIIb. P2 binds to GP IIa III exposing GPla which has no antibody specificity.

In the second preferred method, can separated and collected from platelets with known HLA types. The HLA antigens are extracted from platelets with chloroquine diphosphate-PBS solution at pH5. It is preferred that four volumes of chloroquine solution be mixed with one volume of washed platelets ($3 \times 10^9$ platelets 1 ml) suspended in tris-saline solution. The platelets in solution are then incubated at room temperature for sixty minutes.

The chloroquine/HLA solution is removed from the remainder of the platelets by centrifuging the solution, for example, at 2200g for ten minutes. It is preferred that the chloroquine then be removed from the HLA by column chromatographic techniques, for example, on a G-25 sephadex column. Each of the different types of HLA is collected from platelets of that type. An amount of more than one type of HLA is then added to the wells of a microtiter plate. The plate can be stored, frozen, as indicated above, or it can be desiccated.

In the first and second preferred methods, it is preferred that a panel of HLA types be made. In such a panel at least four wells have the same HLA type. Then the average of the fractions can be compared.

In the practice of this invention, a microtiter plate of either the first type or the second type having previously prepared wells is used to type a patient for HLA or to crossmatch a potential blood recipient for HLA compatibility with potential blood donors. If the plate has been stored frozen, it is first thawed, and the freezing solution is removed. Then the wells are washed twice with 5% human serum albumin (HSA) dissolved in an electrolytically balanced solution, for example, in Isolyte E. After decanting, the wells are again filled with 5% HSA and equilibrated for thirty minutes at room temperature. The wells are decanted and blotted dry.

50 microliters of the serum to be tested are added to each of four wells for each HLA sample. The plate is incubated. One preferred method is floating the plate for one hour in a 37° C. water bath. Then the plate is decanted, blotted, and washed with 2% HSA. Then 100 microliters of a working dilution saline of (Fab')2 anti-human IgG conjugate alkaline phosphatase is added to each well. The uncovered plate is incubated for forty-five minutes at 60° C. Higher temperature may increase false positive readings. The plate is decanted and washed once with 7% HSA. 100 microliters of disodium p-nitrophenyl phosphate (pNp) is added to each well. The pNp solution is made immediately before use, by adding 100 mg pNp to 10 ml of diethanolmine buffer.

The plate is then incubated for thirty minutes at 37° C. in the dark. After the reaction is stopped with 50 microliters of 1M NaOH, the plate is read in an automatic ELISA spectrophotometer.

The present invention can be used to cross match blood between potential recipients and potential donors. In that case a panel is made from the platelets of potential donors and compared to the serum of the potential recipient.

The platelets in a sample of donor blood are isolated by conventional techniques. In general, the techniques involve removing the red and white blood cells from the plasma by centrifugation, then isolating the platelets which are still contained in the plasma by further centrifugation of the plasma. The platelets are washed and a solution of 60,000 platelets per cubic millimeter in citrate-dextrose solution is made. If the platelet density is too low, the solution can be recentrifuged. If it is too high, the solution can be diluted.

Sixty microliters of platelets and sixty microliters of patient serum are added to a microtiter well. Other wells on the microtiter plate, which can be a standard 96 well plate, are used to hold the positive control, the negative control, and a patient direct test control for each crossmatch made. A preferred positive control is pooled plasma from individuals known to react with platelets. A preferred negative control is pooled AB plasma from male volunteers known to have never received blood transfusions.

The wells are then washed with a solution of 5% HSA in isolyte. This allows full coating of the wells and prevents non specific binding by the labeling agent. The wells are washed, then emptied, then new portions of HSA solution are added and the plates incubated.

It is preferred that the label be anti-human IgG/alkaline phosphatase. The label is added to the washed wells, then the dye is added to develop the color in each well. The preferred dye for alkaline phosphatase is pNp. In this test, a positive test indicates an unsuitable crossmatch. A negative test indicates no recipient crossreaction with that particular donor.

The plates are analyzed by detecting the optical densities of each well. One preferred method is the averaging of the values of the optical densities of four crossmatch wells and subtracting the value of the negative control. If the crossmatch is less than some predetermined value for optical density —— for example, 0.245 —— then the cross match is considered acceptable.

One aspect of this invention is a kit for assaying platelets that includes a microtiter plate of either the first type or the second type, or both, and a supply of (Fab '2) anti-human IgG conjugate alkaline phosphatase. It is preferred that such a kit include a supply of pNp phosphate as well.

EXAMPLE I

This example shows the method for making the first microtiter plate. Platelets are collected from donors with known HLA types. Blood is collected in an anticoagulent, preferably ACD-A, and then the platelet-rich plasma (PRP) is obtained by centrifuging the whole blood, at 1030g for five minutes. The upper two-thirds of the PRP is aspirated and centrifuged at 830 g for ten minutes.

The platelet button is then harvested. The platelets are then washed in a modified Tyrodes solution containing 1.5 mg/ml CDI (Sigma Chemical Company, St. Louis). After washing and the platelet count is adjusted to 60000 platelets per mm$^3$. Then sixty microliters of solution is placed in each microtiter well. Platelets of each type are placed in four wells apiece.

The microtiter plates thus prepared can be prepared for long term storage. The plate is treated with a freezing solution, preferably dimethyl sulfoxide (DMSO), heat-inactivated fetal calf serum, and Veronal buffer-ethylene diamine tetraacetic acid (EDTA) and frozen for later use.

It is important to distinguish between HLA antigens and platelet non-specific antigens. The binding of the platelet specific antibodies can be reduced by contacting platelets with a bacterial suspension. The platelets are disrupted by contacting them with Tween - 100 or 1% non-ionic detergent, preferably Noridet P-40 or Triton X-100. Then a formalin fixed protein A containing staphylococcus aureus in approximately 10% suspension is centrifuged and the bacterial suspension pellet is resuspended in 1 ml of the platelet lysate. The bacterial suspension with phosphate buffered saline at pH5 (PBS) before centrifugation. After approximately thirty minutes, the bacteria are centrifuged out of the lysate.

EXAMPLE II

This example shows the method for separating HLA and making an ELISA plate with HLA. Platelets are extracted with chloroquine diphosphate-PBS solution at pH5. Four volumes of chloroquine solution be mixed with one volume of washed platelets (3 × 10$^9$ platelets 1 ml) suspended in tris-saline solution. The platelets in solution are then incubated at room temperature for sixty minutes.

The chloroquine/HLA solution is removed from the remainder of the platelets by centrifuging the solution at 2200g for ten minutes. The chloroquine then be removed from the HLA by column chromatographic techniques, on a G-25 sephadex column. Each of the different types of HLA is collected from platelets of that type. An amount of several different types of HLA are then added to the wells of a microtiter plate. Again four wells are prepared for each type. The plate can be stored, frozen, as indicated above.

EXAMPLE III

This example shows the use of this invention for cross-matching platelets from potential blood recipients with the blood of potential donors. 1.8 ml blood was centrifuged in a Sorvall GLC 4 centrifuge at 2000 RPM for five minutes. The upper two-thirds, the platelet rich plasma, was removed. The removed plasma was centrifuged at 1800 RPM for ten minutes. The resulting platelet button was washed and re-suspended in Isolyte E (McGraw Hill Lab, Irvine, Calif.).

The platelet count was adjusted, by diluting or by recentrifuging, to 60,000 platelets/mm$^3$.

The plates used for the ELISA determination were standard 96-well styrene microtiter plates from Dynatech®. For each crossmatch test, sixty microliters of platelet concentrate were added to two wells for blanks (platelets plus reagents) and to four wells for the test. Four wells were left with no reagents as reagent blank.

The wells were washed with 5% HSA in Isolyte E. The wells were decanted by inverting the plates and more 5% HSA was added. The plates were equilibrated for ten minutes at room temperature. The wells were then decanted and the plate blotted dry with a paper towel.

Human test serum from a potential recipient is added to the wells, the wells are incubated, and then decanted. Then one hundred microliters of working dilution of (Fab '2) anti-human IgG alkaline phosphatase (Jackson Immunoresearch Corp., West Grove Pa.) was added to all wells except the instrument blank wells. Plates were allowed to equilibrate at room temperature for thirty minutes. The wells were decanted, and one hundred microliters of 3.0 mM pNp (Sigma Chemical Company, St. Louis) in diethanolamine buffer was added to each well and incubated in the dark. The reactions were stopped by adding fifty microliters of 1M NaOH.

Immediately after the reaction stopped, the plates were placed into an automatic micro-ELISA spectrophotometer. The optical densities of each plate at 405 nanometers was then determined.

I claim:

1. A kit for assaying platelets comprising;
a plate having a plurality of wells, each well containing a monolayer of platelets of a single type of HLA, said platelets having been previously washed with 1-cyclohexyl-3-(2-morpholinoethyl)-carbodiimide metho-p-toluenesulfonate to thereby enhance bonding between the bottom of each well and the monolayer of platelets contained therein, wherein the plurality of wells contain antigens to more than one type of HLA; and
in a separate container, a supply of (Fab '2) anti-human IgG conjugate alkaline phosphatase.

2. The kit of claim 1, including, in a separate container, a supply of pNp phosphate.

* * * * *